United States Patent [19]

Stannard et al.

[11] Patent Number: 5,869,342
[45] Date of Patent: Feb. 9, 1999

[54] METHOD AND SYSTEM FOR CONTINUOUSLY MONITORING AND CONTROLLING A PROCESS STREAM FOR DECHLORINATION RESIDUAL

[75] Inventors: James W. Stannard, Basking Ridge; Jared K. Bryan, Neptune; Albert Van Grouw, III, North Haledon, all of N.J.

[73] Assignee: Wallace & Tiernan, Belleville, N.J.

[21] Appl. No.: 749,413

[22] Filed: Nov. 18, 1996

Related U.S. Application Data

[63] Continuation of Ser. No. 381,181, Jan. 31, 1995, abandoned, which is a continuation-in-part of Ser. No. 674,244, Mar. 25, 1991, abandoned, and Ser. No. 549,994, Jul. 9, 1990, abandoned, said Ser. No. 674,244, is a continuation-in-part of Ser. No. 549,994.

[51] Int. Cl.$^6$ .................................................. G01N 35/08
[52] U.S. Cl. .............................. 436/55; 436/32; 436/122; 436/125; 210/739; 210/753; 210/764; 422/62; 422/81
[58] Field of Search ..................................... 436/122, 124, 436/125, 52, 55, 149–151; 422/62, 81, 82.01; 210/739, 746, 753, 754, 764, 757

[56] References Cited

U.S. PATENT DOCUMENTS

| | | | |
|---|---|---|---|
| 2,396,934 | 3/1946 | Wallace | 436/125 |
| 2,560,317 | 7/1951 | Wallace | 436/125 |
| 4,271,149 | 6/1981 | Winicov et al. | 424/150 |
| 4,322,215 | 3/1982 | Huber et al. | 422/81 |
| 4,440,726 | 4/1984 | Coulson | 422/82.02 |
| 4,461,711 | 7/1984 | Behrens | 210/757 |
| 4,487,753 | 12/1984 | Massie et al. | 423/573 |
| 4,687,565 | 8/1987 | Hirakata et al. | 204/258 |
| 4,789,638 | 12/1988 | Kramer et al. | 436/111 |
| 4,835,016 | 5/1989 | Rosty et al. | 427/307 |
| 4,957,872 | 9/1990 | Koever et al. | 436/175 |
| 5,232,914 | 8/1993 | Fellman | 514/23 |
| 5,342,490 | 8/1994 | Lever et al. | 204/153.19 |

OTHER PUBLICATIONS

Finger et al., "Development of an on–line zero chlorine residual measurement and control system" J. Water Pollut. Control Fed. (1985) 57(11) 1068–73.

*Primary Examiner*—Jan Ludlow
*Attorney, Agent, or Firm*—Michael, Best & Friedrich

[57] ABSTRACT

A method for determining the amount of residual disinfectant removing agent in a process stream to which the disinfectant removing agent has been added to completely remove a disinfectant residual, comprising the steps of: (a) drawing off a sample of the process stream; (b) mixing an acidic iodate solution and an iodide solution to produce an iodine analyzing agent; (c) adding to the sample the iodine analyzing agent in an amount sufficient to react with the residual disinfectant removing agent and leave an unreacted amount of residual iodine; (d) allowing sufficient time for the iodine to react with the residual disinfectant removing agent; (e) analyzing the sample to determine the amount of residual iodine remaining in the sample, and (f) determining the amount of residual disinfectant removing agent in the sample based on the amount of iodine analyzing agent added and the amount of residual iodine remaining in the sample after reaction.

20 Claims, 1 Drawing Sheet

METHOD AND SYSTEM FOR CONTINUOUSLY MONITORING AND CONTROLLING A PROCESS STREAM FOR DECHLORINATION RESIDUAL

This is a File Wrapper Continuation of application Ser. No. 08/381,181, filed Jan. 31, 1995, now abandoned, which is a continuation in part of application Ser. No. 07/674,244, filed Mar. 25, 1991, now abandoned, which is hereby incorporated by reference. Application Ser. No. 08/381,181 also is a continuation in part of application Ser. No. 07/549,994, filed Jul. 9, 1990, now abandoned, of which application Ser. No. 07/674,244 was a continuation in part, and which is hereby incorporated by reference.

FIELD OF THE INVENTION

This invention relates generally to a method and system for continuously monitoring and controlling a process stream for a dechlorination residual. In particular, the invention relates to a method and system for continuously monitoring and controlling a process stream containing a dechlorination residual by biasing a sample thereof with an analyzing agent to determine the amount of dechlorination residual contained in the process stream. Dechlorination is defined here as the complete or partial removal of any oxidant, including chlorine, by the controlled addition of a reducing agent.

BACKGROUND OF THE INVENTION

Chlorine is commonly used to disinfect sewage treatment plant process streams and for biofouling control in cooling systems. Because chlorine is such a highly effective disinfecting/oxidizing agent, any chlorine unused in the process is just as effective in destroying aquatic life.

In order to eliminate or substantially remove the residual chlorine from a process stream, a dechlorination agent or device is often used. Typically, sulfur dioxide ($SO_2$) is added to the process stream to react quantitatively with the chlorine residual. If $SO_2$ is added in excess of the amount of chlorine residual in the process stream, the chlorine will be completely eliminated.

The amount of unreacted dissolved $SO_2$ (i.e., dechlorination residual) remaining in the process stream is preferably maintained at low, but positive, concentration to insure chlorine residual removal and minimize oxygen consumed. This sort of treatment not only protects aquatic life, but results in more efficient use of the $Cl_2$ and $SO_2$ reagents added to the process stream. However, there are no completely acceptable methods or systems available for directly monitoring and controlling the amount of dechlorination residual in a continuous process stream to which a chlorine disinfectant/oxidant has been previously added.

All of the prior systems are expensive to install and have substantial operational costs associated with maintenance, sample pumping, and reagent costs. These systems are often inherently unstable, producing measurement errors that typically exceed safe regulatory residual limits by several orders of magnitude. This is especially undesirable since dechlorination control continues to be the subject of more stringent government environmental regulations.

Clearly what is needed is a method and system for directly measuring and controlling a continuous process stream for dechlorination residual. The method and system should permit a chlorine residual to be completely eliminated within the process stream while the amount of dechlorination residual is minimized. Monitoring and control should be conducted under conditions where relatively small volumes of the reagent and process sample are used. Moreover, the reagents used should be relatively stable and should not be subject to chemical reaction interferences with other contaminants which may be present within the process stream. The present invention fills that need.

SUMMARY OF THE INVENTION

The invention provides methods and systems for monitoring and controlling the amount of a dechlorination residual or residual disinfectant removing agent such as $SO_2$ in a continuous process stream. The disinfectant removing agent is added in excess to the process stream to reduce or eliminate a disinfectant residual which has previously been added to the process stream.

The methods of the present invention comprise continuously drawing off a sample of the process stream. The sample may have therein a residual disinfectant removing agent such as $SO_2$ or residual disinfectant such as chlorine. An iodine analyzing agent is continuously added to the sample in an amount sufficient to completely react with the residual disinfectant removing agent and leave an unreacted amount of the iodine analyzing agent or, in the case of incomplete disinfectant removal, add to the disinfectant residual. A metered amount of the sample having therein residual disinfectant removing agent is drawn into a metered sample stream by a peristaltic pump for introduction into an analyzer. Metered amounts of an acidic iodate solution and an iodide solution are drawn into a reaction zone by the peristaltic pump and are mixed in the reaction zone to produce the iodine analyzing agent immediately before the iodine analyzing agent is added to the sample. The acidic iodate solution and iodide solution are stored separately before being mixed, so the concentration of iodine in the iodine analyzing agent is stable and $CO_2$ bubbles do not form in the iodine analyzing agent. The iodine analyzing agent is introduced into the sample stream, and a sufficient amount of time is allowed for the iodine to completely react with the residual disinfectant removing agent in the sample. Thereafter, the sample is introduced into the analyzer and continuously analyzed to determine the amount of unreacted or residual iodine, or residual iodine plus iodine produced by any disinfectant in the sample, remaining in the sample. Based on the amount of iodine analyzing agent added, and the amount of residual iodine remaining in the sample after reaction with the residual disinfectant removing agent, the amount of residual disinfectant removing agent or disinfectant residual is determined. Using the determined amount of residual disinfectant removing agent or residual disinfectant, the amount of disinfectant removing agent added to the process stream is controlled. Because the concentration of iodine is stable and no $CO_2$ bubbles are formed in the iodine analyzing agent, a uniform metered amount of the iodine analyzing agent is continuously introduced into the metered sample stream, and the values measured by the analyzer do not fluctuate due to bubbles or similar discontinuities in the iodine analyzing agent. The amount of residual disinfectant removing agent in the sample thus is accurately determined.

The systems of the present invention comprise means for continuously drawing off a sample of the process stream and an analyzer package connected to the sample stream for continuously determining the amount of residual disinfectant removing agent in the sample stream, and thus in the process stream. The analyzer package includes feed means for supplying metered amounts of an acidic iodate solution and a separately stored iodide solution to a reaction zone to produce an iodine solution or iodine analyzing agent immediately before the iodine analyzing agent is added to the metered sample stream and thereafter introduced into the analyzer. The analyzer package includes a peristaltic pump for introducing a uniform metered amount of the iodine analyzing agent into the metered sample stream and for introducing a uniform metered amount of the sample stream into the analyzer. The amount of iodine analyzing agent added to the sample is sufficient to completely react with the residual disinfectant removing agent and leave an unreacted or residual amount of the iodine. The analyzer package includes an analyzer in communication with the sample stream for analyzing the sample containing the residual iodine and for thus determining the amount of residual disinfectant removing agent in the sample. The systems also include controller means which is responsive to an output signal from the analyzer package for continuously and selectably varying the amount of disinfectant removing agent added to the process stream based on the determined amount of residual disinfectant removing agent.

DETAILED DESCRIPTION OF THE INVENTION

Figure 1:
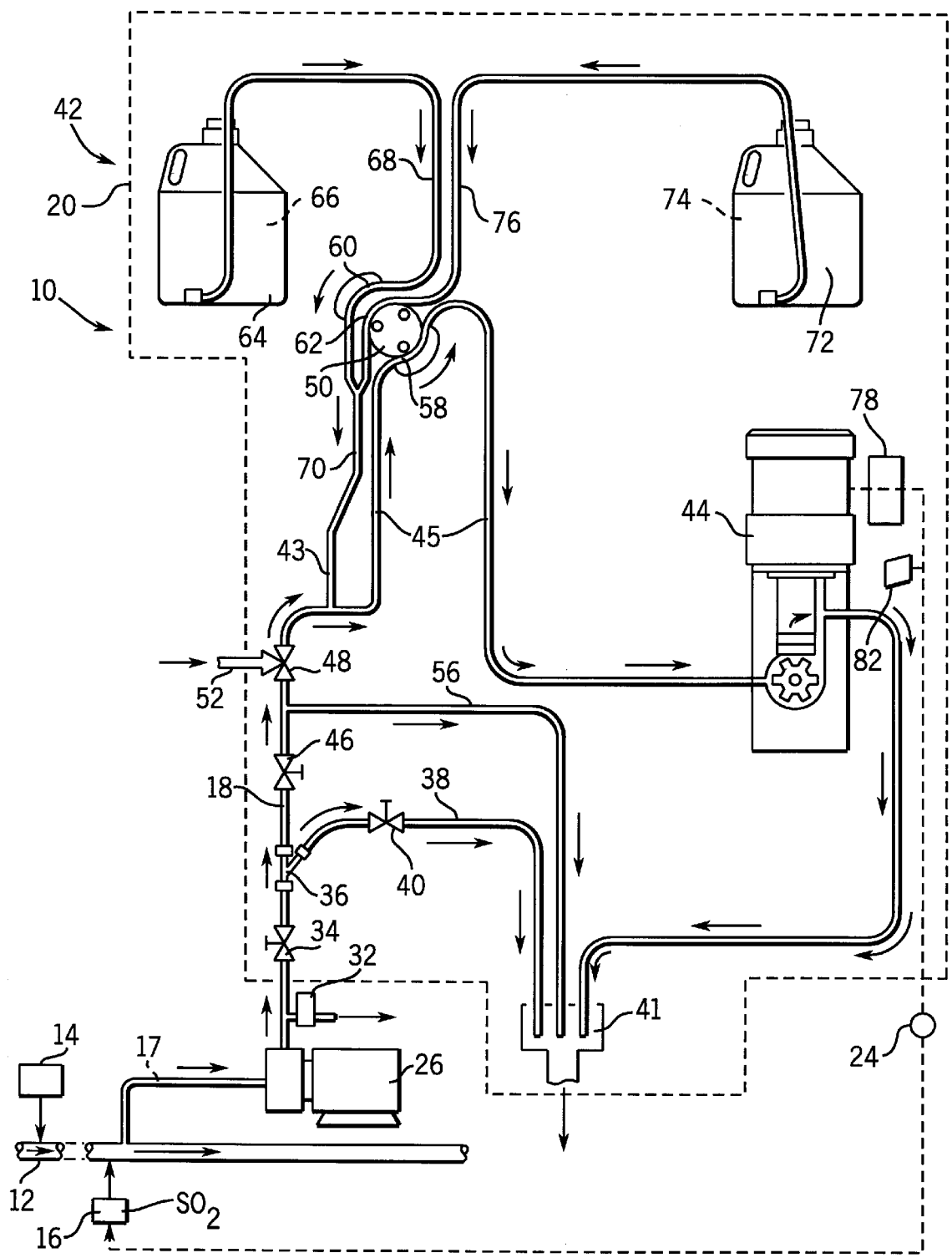
FIG. 1 is a schematic illustration of an embodiment of the method and system of the invention.

There is shown in FIG. 1 a system 10 for monitoring and controlling the amount of residual disinfectant removing agent (i.e., $SO_2$) within a process stream 12. The system 10 includes a supply 14 of a disinfectant or oxidant such as chlorine ($Cl_2$) which is connected to the process stream 12 for introducing chlorine into the process stream 12. Typically, the amount of chlorine introduced into the process stream is in excess of the amount required to disinfect the process stream, and so residual disinfectant or residual chlorine is present downstream from the chlorine supply 14. The system 10 includes a supply of a reducing agent, dechlorination agent or disinfectant removing agent which is connected to the process stream 12 downstream of the chlorine supply 14 for introducing the disinfectant removing agent into the process stream 12. Although other suitable disinfectant removing agents, such as sulfite ($SO_3$—), sodium bisulfite or sodium metasulfite can be used, in the illustrated embodiment the disinfectant removing agent is sulfur dioxide ($SO_2$). The $SO_2$ introduced into the process stream 12 reacts with the chlorine, and thus reduces the amount of residual chlorine in the process stream 12. Ordinarily, the amount of $SO_2$ introduced into the stream is in excess of that necessary to react with and remove all of the residual chlorine in the process stream 12, and thus a dechlorination residual (i.e., residual $SO_2$) is present in the process stream downstream from the $SO_2$ supply 16.

The system 10 includes a sample stream 18 connected to the process stream 12 downstream of the $SO_2$ supply 16 for continuously withdrawing a sample 17 from the process stream 12. The sample stream 18 is connected to an analyzer package 20 for continuously delivering the sample 17 to the analyzer package 20. In the illustrated embodiment, the amount of sample 17 flowing through the sample stream 18 is several thousand milliliters per minute. The system 10 includes the analyzer package 20, which is connected to the sample stream 18 for analyzing the amount of residual $SO_2$ in the sample 17 and thus determining the amount of residual $SO_2$ in the process stream 12. The analyzer package 20 generates an output signal to a controller 24, and thus to the $SO_2$ supply 16, which has a relationship to the amount of residual $SO_2$ determined to be in the process stream. The controller 24 is connected to the analyzer package 20 and receives the output signal from the analyzer package 20. The controller 24 is connected to the $SO_2$ supply 16 and is operable for controlling the amount of $SO_2$ introduced into the process stream 12 in dependence upon the output signal from the analyzer package 20.

The sample 17 is continuously withdrawn from the process stream 12 into the sample stream 18 by the action of a pump 26. The sample stream 18 includes a relief valve 32 for relieving excess pressure in the sample stream 18. The sample stream 18 is connected to the analyzer package 20.

In the illustrated embodiment, the analyzer package 20 includes the elements included within the dashed line boundary. More particularly, the analyzer package includes a portion of the sample stream 18 extending from and including a shut-off valve 34 to and including a three-way valve 48. The sample stream 18 includes the shut-off valve 34 for selectively stopping flow through the sample stream 18. The sample stream 18 includes a Y-strainer 36 for filtering the sample 17 and for removing excess sample from the sample stream 18 through an excess sample stream 38. The excess sample stream 38 includes a control valve 40 for selectively controlling the flow of excess sample through the excess sample stream 38 to a drain 41. The excess sample is collected in the drain 41. In the illustrated embodiment, material collected in the drain 41 is removed as waste. The sample stream 18 includes a second control valve 46 for selectively controlling flow through the sample stream 18 past the Y-strainer 36. The control valves 40 and 46 are operable in conjunction for controlling the proportions of the sample 17 flowing through the sample stream 18 and diverted to the excess sample stream 38.

The sample stream 18 also includes a three-way valve 48 for selectively controlling flow of the sample or calibration water to the sample stream 18. A calibration water stream 52 is connected to the sample stream 18 through the three-way valve 48. The calibration water stream 52 is connectable to supply of calibration water for drawing the calibration water into the sample stream 18. The three-way valve 48 is selectively movable between a first or operating position and a second or calibration position. In the operating position of the three-way valve 48, a sample continuously flows through the three-way valve 48 and the sample stream 18. In the calibration position of the three-way valve 48, calibration water from the calibration water stream 52 flows into the sample stream 18 at the three-way valve 48, and the sample 17 flowing through the sample stream 18 upstream of the three-way valve 48 is diverted through a bypass stream 56 to the drain 42. Typically, the three-way valve 48 is maintained in the operating position for delivering the sample 17 from the sample stream 18 to the metered sample stream 45. When it is desired to calibrate the analyzer package 20, the three-way valve 48 is moved to the calibration position to deliver calibration water into the sample stream 18.

The analyzer package 20 includes feed means 42 for supplying a uniform metered amount of an iodine solution or iodine analyzing agent 43 and a uniform metered amount of the sample 17 to an analyzer 44. The feed means 42 includes a metered sample stream 45. The metered sample stream 45 is connected to the sample stream 18 at the three-way valve 48 and is connected at its opposite end to the analyzer 44. In the illustrated embodiment, flow through the metered sample stream 45 is about twenty five milliliters per minute.

The feed means 42 includes a peristaltic pump 50. The peristaltic pump 50 has separate first, second and third pumping chambers 58, 60 and 62. The first pumping chamber 58 is connected to and forms a portion of the metered sample stream 45. The first pumping chamber 58 continuously supplies a uniform metered amount of the sample through the metered sample stream 45 to the analyzer 44. The second pumping chamber 60 is connected to and forms a portion of an iodate stream 66, as further described below. The third pumping chamber 62 is connected to and forms a portion of an iodide stream 68, as further described below.

The feed means 42 also includes an iodate container or supply 64. The iodate supply 64 has therein an acidic iodate solution 66. An iodate stream 68 is connected to the iodate supply 64 and to a reaction zone 70 via the second pumping chamber 60 of the peristaltic pump 50. The second pumping chamber 60 draws a uniform metered amount of the acidic iodate solution 66 into the iodate stream 68 and delivers the acidic iodate solution 66 into the reaction zone 70. In the illustrated embodiment, flow of the iodate solution 66 through the iodate stream 68 is about six milliliters per hour.

While the acidic iodate solution 66 could be produced in other ways, in a preferred embodiment of the invention, the acidic iodate solution 66 is produced by combining a potassium iodate solution with an acidic buffer material. Although any suitable iodate can be employed, in the illustrated embodiment the iodate is potassium iodate. Any acidic buffering agent can be employed which will react with the iodate and iodide to produce iodine, which will not adversely affect the downstream chemical reaction between the $SO_2$ and iodine, and which will not cause $CO_2$ bubbles to form in the iodine solution. Typically, organic or inorganic acids can be employed for this purpose. Examples of such suitable acidic solutions include, but are not limited to, acetic acid, sulfuric acid, hydrochloric acid, and the like and/or any combination thereof. Although other suitable acidic buffer materials can be used, in the illustrated embodiment the acidic buffer material is an acetic acid solution having a pH of about 4. The acidic iodate solution 66 does not absorb an appreciable amount of $CO_2$.

The acidic iodate solution 66 has a limited shelf-life of about 80 days. In applications where the materials forming the acidic iodate solution 66 are to be stored for a period exceeding the shelf-life of the acidic iodate solution 66, a relatively small volume of concentrated iodate solution can be stored in water, separate from the acidic buffer material. The concentrated iodate solution is stable and will not absorb an appreciable amount of $CO_2$. Similarly, the acidic material will not absorb an appreciable amount of $CO_2$. The small volume of concentrated iodate solution is mixed and diluted with the acidic material to provide the acidic iodate solution 66. The acidic iodate solution 66 then must be used within the period of its shelf-life.

The feed means 42 includes an iodide container or supply 72. The iodide supply 72 has therein an iodide solution 74. An iodide stream 76 is connected to the iodide supply 72 and to the reaction zone 70 via the third pumping chamber 62 of the peristaltic pump 50. The third pumping chamber 62 draws a uniform metered amount of the iodide solution 74 into the iodide stream 76 and delivers the iodide solution 74 into the reaction zone 70. In the illustrated embodiment, flow of the iodide solution 74 through the iodide stream 76 is about six milliliters per hour. Any suitable iodide can be employed which, in an acidic environment, will react with iodate to produce iodine. In the illustrated embodiment, the iodide is potassium iodide. The iodide solution 74 can be formed by dissolving potassium iodide in water. The potassium iodide solution 74 will not absorb an appreciable amount of $CO_2$.

The reaction zone 70 of the feed means 42 is connected to the iodate stream 68 and the iodide stream 76 for receiving uniform metered amounts of the acidic iodate solution 66 and the iodide solution 74. The reaction zone 70 is sufficiently large for the acidic iodate solution 66 and the iodide solution 74 to mix together and react to form a reaction product, e.g. a stream of the iodine solution or iodine analyzing agent 43. The acidic iodate solution 66 and the iodide solution 74 thus react in the reaction zone 70 to form a stream of the iodine analyzing agent 43. It is believed that the reaction is according to the following equation:

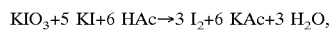

$$KIO_3 + 5\ KI + 6\ HAc \rightarrow 3\ I_2 + 6\ KAc + 3\ H_2O,$$

where the iodate is potassium iodate, the iodide is potassium iodide, and the acid is acetic acid. In other embodiments, different specific iodates, iodides and acids can be used. The pH of the iodine solution 43 is intermediate the pH's of the acidic iodate solution 66 and the iodide solution 74. Thus, no appreciable amount of $CO_2$ will evolve upon combining the acidic iodate solution 66 and the iodide solution 74, and $CO_2$ bubbles and related discontinuities will not form in the iodine analyzing agent 43.

The reaction zone 70 is connected to the metered sample stream 45 for delivering a uniform metered amount of the iodine analyzing agent 43 into the sample 17 in the metered sample stream 45. The iodine analyzing agent 43 is introduced into the metered sample stream 45 immediately after being formed by mixing the acidic iodate solution 66 and the iodide solution 74. The concentration of iodine in the iodine analyzing agent 43 is stable and does not substantially change before the iodine analyzing agent 43 is introduced into the metered sample stream 45. A uniform metered amount of the iodine analyzing agent 43 thus is added into the sample 17 in the metered sample stream 45. Also, the iodine solution 43 thus is delivered to the metered sample stream 45 and to the analyzer 44 in a continuous stream without $CO_2$ bubbles or similar discontinuities.

The metered sample stream 45 is sufficiently large for the iodine analyzing agent 43 and residual $SO_2$ in the sample 17 to completely react and thus reduce the amount of iodine in the sample stream 45. Residual iodine thus remains in the sample in the metered sample stream 45. The metered sample stream 45 is connected to the analyzer 44 via the first pumping chamber 58 of the peristaltic pump 50. The first pumping chamber 58 thus delivers a uniform metered amount of the sample 17 having the residual iodine therein into the analyzer 44 via the metered sample stream 45. A uniform metered amount of the sample 17 having residual iodine therein thus is delivered into the analyzer 44.

The analyzer 44 is connected to the metered sample stream 45 for determining the amount of residual iodine in the sample 17. Although any suitable analyzer can be used to determine the amount of residual iodine in the sample 17, in the illustrated embodiment the analyzer 44 includes an amperometric cell for continuously and directly measuring the amount of residual iodine in the sample 17. The amperometric cell includes three electrodes—a platinum working electrode, a platinum counter-electrode, and a silver/silver chloride reference electrode. The analyzer includes an impeller for mixing the sample 17 therein. It is believed that the reaction at the working electrode is:

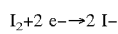

$$I_2 + 2\ e^- \rightarrow 2\ I^-$$

The analyzer includes bias circuitry which compares the potential of the measuring electrode to that of the silver/silver chloride reference electrode and automatically biases the measuring electrode to maintain a fixed potential, and thus screens out interference from contaminants.

The analyzer package 20 also includes means 78 connected to the analyzer 44 for generating an output signal to the controller 24. The output signal is generated in dependence upon the amount of residual iodine measured in the sample by the analyzer 44. In another embodiment, the means 78 for generating an output signal can be an integral portion of the circuitry of the analyzer 44.

In the illustrated arrangement, the analyzer package 20 also includes visual display means 82, such as an LCD display, for displaying the output signal 22. In another embodiment, the visual display means can be omitted.

In the illustrated embodiment, the analyzer package 20 includes the excess sample stream 38, drain 41, a portion of the sample stream 18, Y-strainer 36, control valves 34, 40 and 46, internal bypass stream 56, three-way valve 48, calibration water stream 52, metered sample stream 45, peristaltic pump 50, iodate supply 64, iodate stream 68, iodide supply 72, iodide stream 76, analyzer 44, means 78 for generating an output signal, and visual display means 82. In other embodiments, the analyzer package can include different elements of the system. For example, the analyzer package may include the controller 24. Also for example, in some embodiments, the analyzer package may not include the sample stream 18, Y-strainer 36, excess sample stream 38, drain 41, iodate supply 64, iodide supply 72 or the means 78 for generating an output signal.

The controller 24 is connected to the means 78 for generating an output signal, for receiving the output signal from the analyzer package 20. The controller 24 also is connected to the $SO_2$ supply 16 for controlling the amount of $SO_2$ added to the process stream 12 in dependence upon the output signal from the analyzer 52. In another embodiment, the controller 24 can be connected to another stream instead of the $SO_2$ supply, such as the process stream or the chlorine supply, for controlling the flow rate of the respective stream.

In operation of the system, chlorine (i.e., the disinfectant) is introduced into the process stream 12 at the chlorine supply 14 to disinfect the process stream. Introduction of the chlorine to disinfect the process stream typically results in residual chlorine being introduced into the process stream. Downstream from the chlorine supply 14, the $SO_2$ is introduced into the process stream 12 in order to remove residual chlorine from the process stream. Downstream from the $SO_2$ supply 16, the sample stream 18 is continuously withdrawn from the process stream 12 in order to determine the amount of residual $SO_2$ remaining in the process stream 12 after dechlorination.

The sample stream 18 is withdrawn from the process stream 12 by action of the pump 26. A uniform metered amount of the sample 17 is drawn into the metered sample stream 45 by the first pumping chamber 58 of the peristaltic pump 50. A uniform metered amount of the acidic iodate solution 66 is drawn into the iodate stream 68 and into the reaction zone 70 by the second pumping chamber 60. A uniform metered amount of the iodide solution 74 is drawn into the iodide stream 76 and into the reaction zone 70 by the third pumping chamber 62. The acidic iodate solution 66 and the iodide solution 74 react in the reaction zone 70 to form a stream of the iodine analyzing agent 43. The acidic iodate solution 66, the iodide solution 74 and the iodine analyzing agent 43 do not absorb $CO_2$, and so $CO_2$ bubbles or similar discontinuities do not form in the iodine analyzing agent 43. A uniform metered amount of the iodine analyzing agent 43 thus is continuously added into the sample 17 in the metered sample stream 45 from the reaction zone 70 immediately after the iodine analyzing agent is formed in the reaction zone 70. The iodine analyzing agent 43 and sample 17 react in the metered sample stream 45 and thus reduce the amount of iodine analyzing agent 43 in the sample stream 45. A uniform metered amount of the sample 17 having therein a residual amount of the iodine is delivered into the analyzer 44 by the first pumping chamber 58, via the metered sample stream 45. The amount of residual iodine in the sample 17 is continuously measured in the analyzer 44. An output signal 22 is generated in dependence upon the amount of residual iodine measured in the sample by the analyzer 44, and the amount of $SO_2$ added to the process stream 12 is controlled in dependence upon the output signal from the analyzer 44 by the controller 24. The system 10 thus continuously monitors and controls the amount of disinfectant removing agent, and the amount of residual disinfectant, in the process stream.

It has been found that, in other prior arrangements, fluctuations or "noise" in the values measured by the analyzer can be caused by $CO_2$ bubbles or similar discontinuities present in the iodine analyzing agent added to the metered sample stream and thereafter introduced into the analyzer. Prior arrangements thus have required a gas purger to eliminate $CO_2$ bubbles. The present invention avoids $CO_2$ bubbles or similar discontinuities being introduced into the iodine analyzing agent 43 and the metered sample stream 45, and thus does not include a gas purger. The system 10 thus also avoids fluctuations or "noise" in the values measured by the analyzer which might otherwise result from such $CO_2$ bubbles or similar discontinuities. It is believed that the accuracy of the output signal 80 in relation to the amount of unreacted or residual iodine in the sample 17 is dependent upon whether a uniform metered amount of the iodine analyzing agent 43 is continuously introduced into the metered sample stream 45, and also upon whether a uniform metered amount of the metered sample stream 45 is continuously introduced into the analyzer 44. It is also believed that the accuracy of the output signal 80 is improved by continuously introducing a uniform, uninterrupted stream of the iodine analyzing agent 43 into the metered sample stream 45 and by continuously introducing a uniform, uninterrupted stream of the metered sample stream 45 into the analyzer 44.

A uniform metered amount of the iodine analyzing agent 43 is continuously added to the metered sample stream 45 and thus continuously delivered to the analyzer 44 in a uniform metered amount without $CO_2$ bubbles or similar discontinuities. The iodine analyzing agent 43 includes a stable concentration of iodine and does not have therein $CO_2$ bubbles or similar discontinuities, so a uniform metered amount of the metered sample stream 45 having residual iodine therein is continuously delivered to the analyzer 44 by the peristaltic pump 50. The sample 17 is delivered to the analyzer 44 without such $CO_2$ bubbles or discontinuities, and the values measured by the analyzer 44 thus do not fluctuate or include "noise" due to such bubbles or discontinuities. In turn, the amount of residual $SO_2$ determined to be in the process stream 12 does not fluctuation or include "noise" due to such bubbles or discontinuities, and the amount of $SO_2$ in the process stream 12 is accurately controlled.

In practicing the invention, the flow rate and concentration of the acidic iodate solution, the iodide solution, and the iodine analyzing agent depend, in part, upon many different variables. Examples of variables which should be taken into consideration when determining the flow rates and concentrations of the acidic iodate solution, the iodide solution, and the iodine analyzing agent include, but are not limited to, the flow rate of the sample 17 in the metered sample stream 45, the specific composition, normality and pH of the acidic iodate solution 66 and the iodide solution 74; the amount of time required for the specific iodate, iodide, and acidic solution to react with one another and thus form the iodine analyzing agent; the stoichiometric amount of iodine necessary for reaction with the disinfectant removing agent; and the like. One skilled in the art will be able to determine the flow rates and concentrations of the acidic iodate solution 66 and the iodide solution 74, and the flow rates of the sample stream 18 and metered sample stream 45 to be employed.

The conditions in the foregoing description are for illustration only and should not be construed as limiting the scope of the invention. The present invention may be embodied in other specific forms without departing from the spirit or essential attributes thereof, and accordingly, reference should be made to the appended claims, rather than to the foregoing specification, as indicating the scope of the invention.

What is claimed is:

1. A method for controlling the amount of a residual disinfectant removing agent in a continuous process stream into which a disinfectant and the disinfectant removing agent have been added comprising the steps of:

(a) providing a sample system including a reaction zone, a first source of a first solution containing an iodate component and an acidic component connected in fluid communication with said reaction zone, a second source of a second solution containing an iodide component capable of reacting with the iodate and acidic components to produce iodine connected in fluid communication with said reaction zone, and means for continuously withdrawing a sample stream from the process stream wherein said sample stream is in fluid communication with said reaction zone;

(b) continuously introducing into said reaction zone predetermined amounts of said first and second solutions from said first and second sources, respectively, to produce an analyzing agent containing a predetermined concentration of iodine, said analyzing agent being substantially free of $CO_2$;

(c) continuously introducing into said sample stream from said reaction zone a predetermined amount of said analyzing agent sufficient to completely react with the residual disinfectant removing agent in said sample stream and leave an amount of unreacted iodine;

(d) continuously analyzing said sample stream downstream from said reaction zone to determine the amount of unreacted iodine therein;

(e) continuously determining the amount of residual disinfectant removing agent in said sample stream based on the amount of said analyzing agent added and the amount of unreacted iodine; and (f) continuously adjusting the amount of disinfectant removing agent added to the process stream based on the amount of residual disinfectant removing agent in said sample stream.

2. The method of claim 1, wherein steps (b), (c), (d), (e) and (f) occur substantially simultaneously.

3. The method of claim 1, wherein the disinfectant includes chlorine.

4. The method of claim 1, wherein the residual disinfectant removing agent includes sulphur dioxide.

5. A method for controlling the amount of a residual disinfectant removing agent in a continuous process stream into which a disinfectant and the disinfectant removing agent have been added comprising the steps of:

(a) providing a sample system including a reaction zone, a first source of a first solution containing an iodate component and an acidic component connected in fluid communication with said reaction zone, a second source of a second solution containing an iodide component capable of reacting with the iodate and acidic components in said first solution to produce iodine connected in fluid communication with said reaction zone, and means for continuously withdrawing a sample stream from the process stream such that said sample stream is in fluid communication with said reaction zone;

(b) continuously introducing into said reaction zone said sample stream and predetermined amounts of said first and second solutions from said first and second sources, respectively, to produce a predetermined amount of analyzing agent containing a predetermined concentration of iodine sufficient to completely react with the residual disinfectant removing agent in said sample stream and leave an amount of unreacted iodine, said analyzing agent being substantially free of $CO_2$;

(c) continuously analyzing said sample stream downstream from said reaction zone to determine the amount of unreacted iodine therein;

(d) continuously determining the amount of residual disinfectant removing agent in said sample stream based on the amount of said analyzing agent added and the amount of unreacted iodine; and (e) adjusting the amount of disinfectant removing agent added to the process stream based on the amount of residual disinfectant removing agent in said sample stream.

6. The method of claim 5, wherein steps (b), (c), (d), (e) and (f) occur substantially simultaneously.

7. The method of claim 5, wherein the disinfectant includes chlorine.

8. The method of claim 5, wherein the residual disinfectant removing agent includes sulphur dioxide.

9. An apparatus for controlling the amount of a residual disinfectant removing agent in a continuous process stream into which a disinfectant and the disinfectant removing agent have been added, comprising:

a reaction zone;

a first source of a first solution containing an iodate component and an acidic component, said first source connected in fluid communication with said reaction zone;

a second source of a second solution containing an iodide component capable of reacting with the iodate component and the acidic component in said first solution to produce an analyzing agent that is reactive with the disinfectant removing agent and substantially free of $CO_2$, said second source connected in fluid communication with said reaction zone;

means for continuously withdrawing a sample stream from the process stream such that said sample stream is in fluid communication with said reaction zone;

means for continuously introducing into said reaction zone a predetermined amount of said first and second solutions from said first and second sources, respectively, to produce a predetermined concentration of said analyzing agent;

means for continuously introducing into said sample stream from said reaction zone a predetermined amount of said analyzing agent sufficient to completely react with the residual disinfectant removing agent in said sample stream and leave an amount of unreacted analyzing agent;

an analyzer in operable communication with the sample stream for analyzing said sample stream downstream from said reaction zone to determine the amount of unreacted analyzing agent therein;

means for continuously determining the amount of residual disinfectant removing agent in said sample stream based on the amount of said analyzing agent added and the amount of unreacted analyzing agent; and means for continuously adjusting the amount of disinfectant removing agent added to the process stream based on the amount of residual disinfectant removing agent in said sample stream.

10. The apparatus of claim 9, wherein the disinfectant includes chlorine.

11. The apparatus of claim 9, wherein the residual disinfectant removing agent includes sulphur dioxide.

12. The apparatus of claim 9, wherein the analyzing agent includes iodine.

13. The apparatus of claim 9, wherein the first and second sources, the reaction zone, the sample stream, and the analyzer are in fluid communication such that a predetermined amount of analyzing agent is produced in the reaction chamber, a predetermined amount of analyzing agent is fed into the sample stream, and a portion of the sample stream is analyzed substantially simultaneously.

14. The apparatus of claim 9, wherein said means for continuously introducing into said reaction zone includes a peristaltic pump.

15. The apparatus of claim 14, wherein said means for continuously introducing into said sample stream includes said peristaltic pump.

16. A method for controlling the amount of a residual disinfectant removing agent in a continuous process stream into which a disinfectant and the disinfectant removing agent have been added comprising the steps of:

(a) providing a sample system including a reaction zone, a first source of a first solution containing a first reactant and an acidic component in fluid communication with said reaction zone, a second source of a second solution containing a second reactant capable of reacting with the first reactant and the acidic component in said first solution to produce an analyzing agent that is reactive with the disinfectant removing agent connected in fluid communication with said reaction zone, and means for continuously withdrawing a sample stream from the process stream wherein said sample stream is in fluid communication with said reaction zone;

(b) continuously introducing into said reaction zone predetermined amounts of said first and second solutions from said first and second sources, respectively, to continuously produce a predetermined amount of said analyzing agent, said analyzing agent being substantially free of $CO_2$;

(c) continuously introducing into said sample stream from said reaction zone a predetermined amount of said analyzing agent sufficient to completely react with the residual disinfectant removing agent in said sample stream and leave an amount of unreacted analyzing agent;

(d) continuously analyzing said sample stream downstream from said reaction zone to determine the amount of unreacted analyzing agent therein;

(e) continuously determining the amount of residual disinfectant removing agent in said sample stream based on the amount of said analyzing agent added and the amount of unreacted analyzing agent; and (f) continuously adjusting the amount of disinfectant removing agent added to the process stream based on the amount of residual disinfectant removing agent in said sample stream.

17. The method of claim 16, wherein steps (b), (c), (d), (e) and (f) occur substantially simultaneously.

18. The method of claim 16, wherein the disinfectant is chlorine.

19. The method of claim 16, wherein the residual disinfectant removing agent is sulphur dioxide.

20. The method of claim 16, wherein the analyzing agent includes iodine.

* * * * *